United States Patent
Thomissen et al.

(10) Patent No.: US 7,351,820 B2
(45) Date of Patent: Apr. 1, 2008

(54) PROCESS FOR PREPARING CAPROLACTAM BY BECKMANN REARRANGEMENT

(75) Inventors: Petrus Jozef Hubertus Thomissen, Lanaken (BE); Joannes Albertus Wilhelmus Lemmens, Roermond (NL); Theodorus Maria Smeets, Elsloo (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/557,771

(22) PCT Filed: May 17, 2004

(86) PCT No.: PCT/EP2004/005340

§ 371 (c)(1),
(2), (4) Date: Nov. 29, 2006

(87) PCT Pub. No.: WO2004/103963

PCT Pub. Date: Dec. 2, 2004

(65) Prior Publication Data

US 2007/0083043 A1    Apr. 12, 2007

(30) Foreign Application Priority Data

May 23, 2003 (EP) .................. 03076589
May 23, 2003 (EP) .................. 03076590
May 23, 2003 (EP) .................. 03076591
May 23, 2003 (EP) .................. 03076592

(51) Int. Cl.
*C07D 201/04* (2006.01)
(52) U.S. Cl. ...................................... 540/535
(58) Field of Classification Search ................. 540/535
See application file for complete search history.

(56) References Cited

U.S. PATENT DOCUMENTS 2,237,365 A  4/1941  Schlack et al.
3,914,217 A  10/1975 Smith
3,953,438 A  4/1976  Koppel

FOREIGN PATENT DOCUMENTS

EP    0 785 188    7/1997

OTHER PUBLICATIONS

U.S. Appl. No. 10/557,753, filed Nov. 21, 2005.

*Primary Examiner*—Bruck Kifle
(74) *Attorney, Agent, or Firm*—Nixon & Vanderhye P.C.

(57) ABSTRACT

The invention relates to a process for preparing caprolactam by Beckmann rearrangement of cyclohexanone oxime by feeding cyclohexanone oxime to a reaction mixture comprising (i) sulfuric acid (ii) $SO_3$ and (iii) caprolactam, wherein the $SO_3$ content of the reaction mixture is between 9 and 20 wt. % and the molar ratio M of the reaction mixture defined as $(n_{so3}+n_{H2SO4})/n_{cap}$ is between 1 and 1.4, wherein
$n_{so3}$=quantity of $SO_3$ in reaction mixture, in mol
$n_{so3}$=quantity of $H_2SO_4$ in reaction mixture, in mol
$n_{cap}$=quantity of caprolactam in reaction mixture, in mol.

7 Claims, 2 Drawing Sheets

PROCESS FOR PREPARING CAPROLACTAM BY BECKMANN REARRANGEMENT

Figure 1:
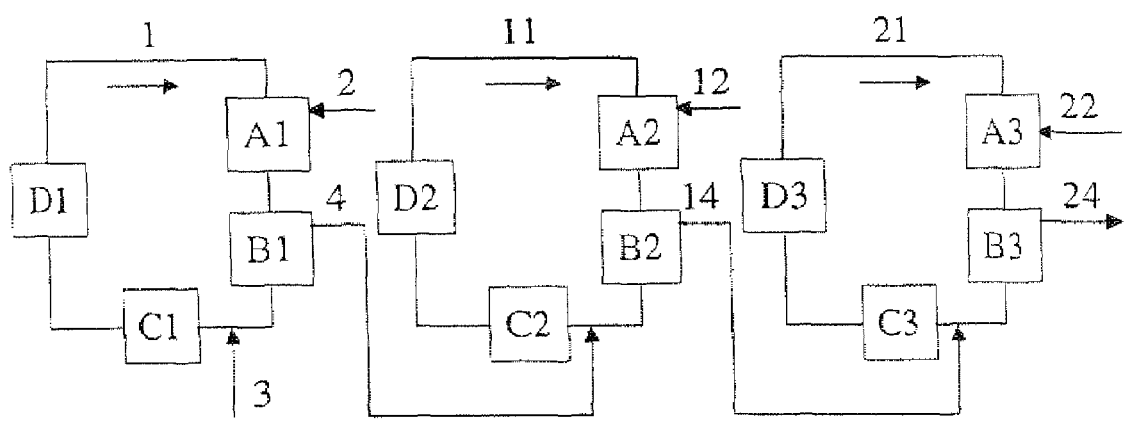

This application is the US national phase of international application PCT/EP2004/005340 filed 17 May 2004 which designated the U.S. and claims benefit of EP 03076590.3, EP 03076591.1, EP 03076589.5 and EP 03076592.9, dated 23 May 2003, respectively, the entire content of which is hereby incorporated by reference.

FIELD OF INVENTION

The invention relates to a process for preparing caprolactam by Beckmann rearrangement of cyclohexanone oxime by feeding cyclohexanone oxime to a reaction mixture comprising (i) sulfuric acid (ii) $SO_3$ and (iii) caprolactam.

BACKGROUND AND SUMMARY OF INVENTION

Caprolactam can be prepared by Beckmann rearrangement of cyclohexanone oxime. Such Beckmann rearrangement can be carried out by admixing cyclohexanone oxime to a reaction mixture comprising caprolactam, sulfuric acid and $SO_3$. In such process the sulfuric acid and $SO_3$ is a catalyst for the conversion of cyclohexanone oxime towards caprolactam. Such conversion is known to occur instantaneously.

Such a process is for example described in U.S. Pat. No. 3,914,217. In the process as described in U.S. Pat. No. 3,914,217 the Beckmann rearrangement is carried out in three stages in series. Cyclohexanone oxime is fed to each stage containing a circulating rearrangement mixture having a sulfuric acid+$SO_3$ to caprolactam weight ratio and a $SO_3$ content within certain ranges. The circulating rearrangement mixture of the first stage has a sulfuric acid+$SO_3$ to caprolactam weight ratio of 1.33 to 1.80 (molar ratio of 1.55 to 2.17) and a $SO_3$ content of 2 to 14 wt. %; the circulating rearrangement mixture of the second stage has a sulfuric acid+$SO_3$ to caprolactam weight ratio of 1.14 to 1.31 (molar ratio of 1.32 to 1.55) and a $SO_3$ content of at least 0.82 wt. %, preferably 0.82 to 6.5 wt. % and the circulating rearrangement mixture of the third stage has a sulfuric acid+$SO_3$ to caprolactam weight ratio of 1.00 to 1.13 (molar ratio of 1.15 to 1.33) and a $SO_3$ content of at least 0.4 wt. %, preferably 0.4 to 4 wt. %. The reaction mixture obtained in the third rearrangement stage essentially containing caprolactam, sulfuric acid and optionally residual sulfur trioxide is sent to a reactor system together with ammonia, water and a solvent such as toluene. The sulfuric acid and $SO_3$ are neutralized by converting the sulfuric acid and $SO_3$ into ammonium sulfate and the caprolactam is simultaneously extracted from the ammonium sulfate solution formed in this system.

It is known that rearrangement can be effected at various values for the molar ratio M. This is in particular the case for the so-called more stage rearrangement in which the molar ratio M of the reaction mixture decreases in each further step.

However, it has been found that in the process as for example described in U.S. Pat. No. 3,914,217 the yield to caprolactam is still low when working at low molar ratio.

As used herein, the molar ratio M of the reaction mixture is defined as $(n_{SO3}+n_{H2SO4})/n_{cap}$, wherein $n_{SO3}$=quantity of $SO_3$ in reaction mixture, in mol (1 mol $SO_3$ corresponds with 80 g), $n_{H2SO4}$=quantity of $H_2SO_4$ in reaction mixture, in mol (1 mol $H_2SO_4$ corresponds with 98 g) and $n_{cap}$=quantity of caprolactam in reaction mixture, in mol (1 mol caprolactam corresponds with 113 g). As used herein, with $SO_3$ content (wt. %) is meant the amount of $SO_3$ (g) relative to the total amount (g) of reaction mixture comprising sulfuric acid, $SO_3$ and caprolactam. With $SO_3$ is meant $SO_3$ which can be analyzed as such in the reaction mixture.

The object of the invention is a process for preparing caprolactam by Beckmann rearrangement of cyclohexanone oxime with an improved yield to caprolactam when working at low molar ratio.

This object is achieved in that the $SO_3$ content of the reaction mixture is between 9 and 20 wt. % and the molar ratio M of the reaction mixture defined as $(n_{SO3}+n_{H2SO4})/n_{cap}$ is between 1 and 1.4, wherein
$n_{SO3}$=quantity of $SO_3$ in reaction mixture, in mol
$n_{H2SO4}$=quantity of $H_2SO_4$ in reaction mixture, in mol
$n_{cap}$=quantity of caprolactam in reaction mixture, in mol.

It has been found that with the process of the invention the yield of the rearrangement of cyclohexanone oxime to caprolactam is improved. Working at low molar ratio is advantageous as it results in the formation of less ammonium sulfate during subsequent neutralization.

In the process of the invention, by-products produced to a lesser extent resulting in an improved quality of the obtained caprolactam.

It has also surprisingly been found that, in spite of the high amounts of $SO_3$, the caprolactam quality is not negatively influenced.

As used herein, the $SO_3$ content (wt. %) is given relative to the weight of the reaction mixture comprising sulfuric acid, $SO_3$ and caprolactam.

BRIEF DESCRIPTION OF THE ACCOMPANYING DRAWINGS

Figure 2:
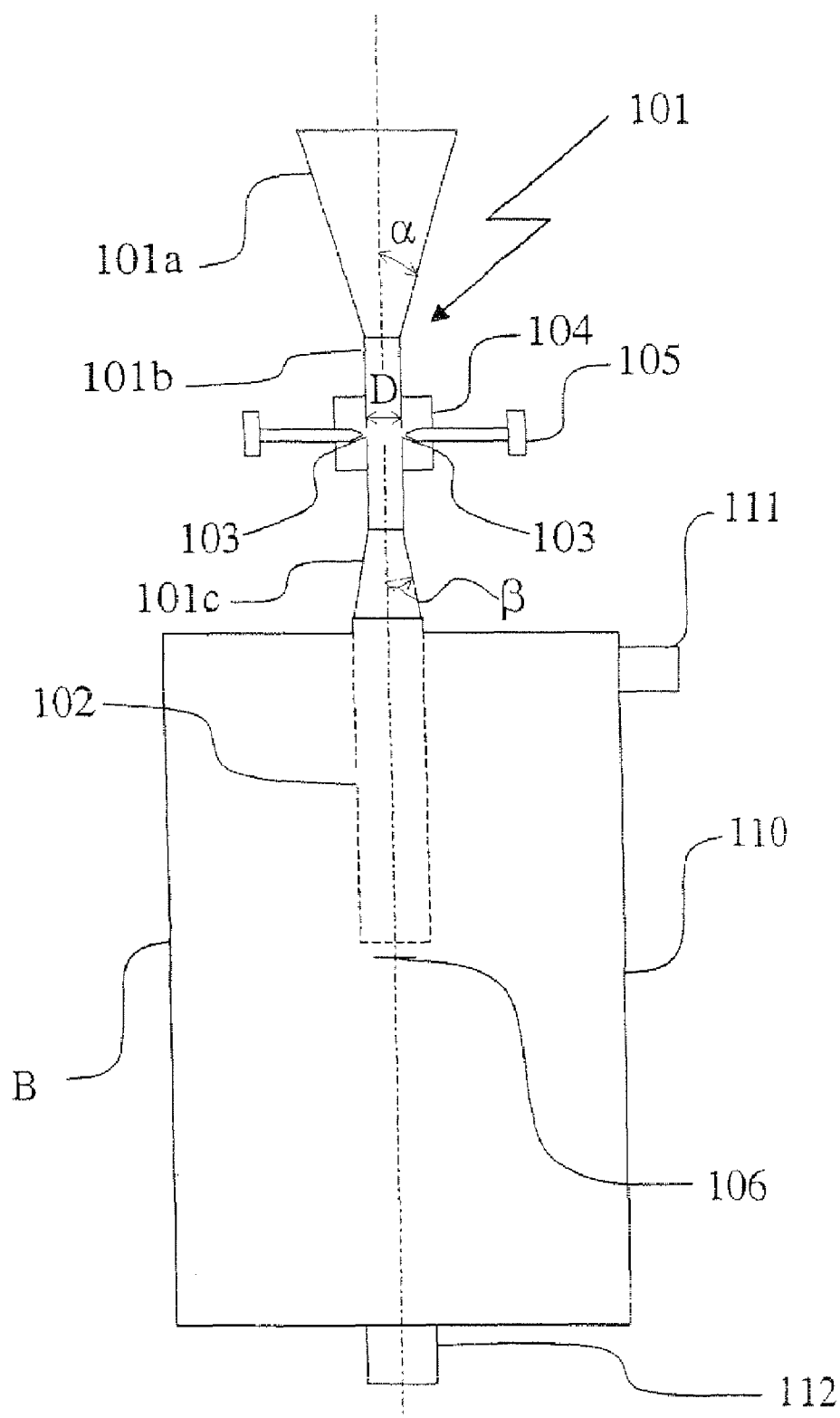

FIG. 1 is a schematic diagram of a three-stage Beckman rearrangement process for preparing caprolactam according to an embodiment of the invention; and FIG. 2 is a schematic view of a mixing device that is preferably used as the mixing devices A1, A2 and A3 depicted in FIG. 1.

DETAILED DESCRIPTION OF THE INVENTION

According to the invention, cyclohexanone oxime is introduced into a reaction mixture comprising sulfuric acid, $SO_3$ and caprolactam having a molar ratio of between 1 and 1.4 and a $SO_3$ content of between 9 and 20 wt. %, preferably higher than 10 wt. % $SO_3$, more preferably higher than 12 wt. % and preferably lower than 18 wt. %. Preferably, the molar ratio M of the reaction mixture is between 1.15 and 1.4 and the $SO_3$ content of the reaction mixture is between 9 and 20 wt. %, preferably higher than 10 wt. %, more preferably higher than 12 wt. % and preferably lower than 18 wt. %. As used herein, the values for M and the concentration of $SO_3$ and the temperature of the reaction mixture refer in particular to the values in the reaction mixture obtained after feeding of the cyclohexanone oxime into the reaction mixture. The values for M and the $SO_3$ content may be obtained in any suitable way. In a preferred embodiment, the process is a continuous process, said process preferably comprising keeping the reaction mixture in circulation, feeding a mixture comprising sulfuric acid and $SO_3$, for instance oleum or a reaction mixture comprising caprolactam, sulfuric acid and $SO_3$ to the circulating reaction mixture, and withdrawing part of the circulating reaction mixture. The amount of mixture comprising sulfuric acid and $SO_3$, the $SO_3$ content thereof, the amount of cyclohexanone oxime fed to the circulating reaction mixture and the water content of the oxime fed to the circulating reaction mixture may be chosen such that M and the $SO_3$ content of the reaction mixture have the preferred values. Oleum may have any suitable $SO_3$ concentration, for instance 18 to 35 wt. % $SO_3$.

Preferably, cyclohexanone oxime is introduced into the reaction mixture having a water content of less than 2 wt. %, more preferably less than 1 wt. %, preferably less than 0.2 wt. % and even more preferably less than 0.1 wt. %. Feeding cyclohexanone oxime having such low water content is advantageous as it provides an effective way of obtaining a reaction mixture having a $SO_3$ content of higher than 9 wt. %, while the addition of large quantities of $SO_3$ is not needed. Adding cyclohexanone oxime having such water content makes it possible to perform the Beckmann rearrangement at low molar ratio and at the same time at high $SO_3$ content, while the addition of large quantities of $SO_3$ is not needed. Performing the Beckmann rearrangement at low molar ratio and high $SO_3$ content is advantageous since it results in that the yield to caprolactam is improved while the amount of ammonium sulfate during subsequent neutralisation is not increased (same molar ratio). Additionally, high amounts of $SO_3$ at such low molar ratio results in an improved quality of the obtained caprolactam.

The temperature at which the Beckmann rearrangement in a reaction mixture having a molar ratio of between 1 and 1.4 and a $SO_3$ content of between 9 and 20 wt. % is carried out may have any suitable value. Preferably, the temperature is between 70 and 130° C., more preferably the temperature is between 80 and 120° C.

In a preferred embodiment, the rearrangement is carried out in a plurality of stages connected in series in which the molar ratio M of the reaction mixture preferably decreases in each further stage (herein after referred to as more stage rearrangemt). Preferably, the rearrangement is carried out in at least two and more preferably in at least three stages connected in series. Each of these stages is charged with cyclohexanone oxime, while preferably all the oleum required is charged into the first stage. Advantageously, cyclohexanone oxime is fed to each stage with an amount decreasing from stage to stage. This is advantageous as, due to the lower molar ratio in each further stage, the yield to caprolactam decreases in each further stage. Feeding cyclohexanone oxime to each stage with an amount decreasing from each stage results in that the overall high yield to caprolactam is maintained with a comparable amount of ammonium sulphate by-product formation. In a more stage rearrangement, the Beckmann rearrangement in each stage is preferably carried out in a circulating reaction mixture comprising caprolactam, sulfuric acid and $SO_3$ by continuously feeding cyclohexanone oxime and, separately therefrom, oleum (first stage) resp. the amount of the circulating reaction mixture withdrawn from the previous stage (if any) to the circulating reaction mixture and by continuously withdrawing an amount of the circulating reaction mixture equivalent to the amount of cyclohexanone oxime and the amount of oleum (first stage) resp. the amount of the circulating reaction mixture withdrawn from the previous stage (if any) introduced to the circulating reaction mixture and by continuously feeding said amount to the next stage (if any). In the last stage of a more stage rearrangement a portion of the circulating reaction mixture is preferably withdrawn equivalent to the amount of cyclohexanone oxime and the amount of the circulating reaction mixture withdrawn from the previous stage and introduced into the circulating reaction mixture of the last stage; from said portion caprolactam is recovered. Preferably, oleum is continuously introduced into the circulating reaction mixture of the first stage in an amount sufficient to maintain the molar ratio M of the circulating reaction mixture in at least the last stage of the more stage rearrangement between 1 and 1.4. Working at such low molar ratio and high $SO_3$ content in especially the last stage of a more stage rearrangement is advantageous as low molar ratios in the last stage of a more stage rearrangement results in the formation of small amounts of ammonium sulfate during subsequent neutralisation while high amounts of $SO_3$ at such low molar ratio results in an improved yield to caprolactam and additionally results in an improved quality of the obtained caprolactam.

In one preferred embodiment of the invention, the rearrangement is carried out in two stages connected in series. In this embodiment, caprolactam is preferably obtained by a continuous process comprising a) feeding (i) oleum and (ii) cyclohexanone oxime into a first reaction mixture comprising caprolactam, sulfuric acid and $SO_3$, b) feeding (iii) a portion of the first reaction mixture and (iv) cyclohexanone oxime into a second reaction mixture comprising caprolactam, sulfuric acid and $SO_3$, wherein the molar ratio M of the second reaction mixture is between 1.0 and 1.4 and the $SO_3$ content of the second reaction mixture is between 9 and 20 wt. %, and c) withdrawing a portion of the second reaction mixture from which caprolactam is recovered. Preferably, the first and second reaction mixture are kept in circulation.

In an even more preferred embodiment of the invention, the rearrangement is carried out in three stages connected in series. In this embodiment, caprolactam is obtained by a continuous process comprising a) feeding (i) oleum and (ii) cyclohexanone oxime into a first reaction mixture comprising caprolactam, sulfuric acid and $SO_3$, b) feeding (iii) a portion of the first reaction mixture and (iv) cyclohexanone oxime into a second reaction mixture comprising caprolactam, sulfuric acid and $SO_3$, c) withdrawing a portion of the second reaction mixture, d) feeding (v) a portion of the second reaction mixture and (vi) cyclohexanone oxime into a third reaction mixture comprising caprolactam, sulfuric acid and $SO_3$, wherein the molar ratio M of the third reaction mixture is between 1.0 and 1.4 and the $SO_3$ content of the third reaction mixture is between 9 and 20 wt. %, and e) withdrawing a portion of the third reaction mixture from which caprolactam is recovered. Preferably, the first, second and third reaction mixture are kept in circulation.

It has been found that an effective way of performing a two stage or three stage rearrangement, in which the second or third circulating rearrangement mixture has a molar ratio M of between 1.0 and 1.4 and a $SO_3$ content of between 9 and 20 wt. %, is to introduce cyclohexanone oxime in said rearrangement mixture, said cyclohexanone oxime having a water content of less than 2% by weight, preferably less than 1 wt. % water, preferably less than 0.2 wt. %and even more preferably less than 0.1 wt. %. Using cyclohexanone oxime having a water content of less than 2% by weight is advantageous because the use of cyclohexanone oxime with such a small amount of water results in that such a low molar ratio in combination with a high $SO_3$ content can be obtained without having to add high quantities of $SO_3$. Adding high quantities of $SO_3$ is disadvantageous, since, either a high $SO_3$ concentration in the oleum ($H_2SO_4$/$SO_3$ mixture) has to be applied, which is disadvantageous from an economical point of view and because the risk of fuming of the oleum increases and because the flowability of the oleum decreases, or, when still using a relatively low concentration of $SO_3$ in the oleum, high quantities of oleum has to be fed to the rearrangement mixture per quantity of oxime, which results in the formation of high amounts of by-product (ammonium sulfate) during subsequent neutralization. Introducing cyclohexanone oxime having such a low water content is advantageous as either a higher yield to caprolactam can be obtained for a given amount of $SO_3$ added to the process, or less $SO_3$ needs to be added to obtain a given yield to caprolactam. In addition, introducing cyclohexanone oxime having such a low water content is advantageous as either an improved quality of the obtained caprolactam can be obtained for a given amount of $SO_3$ added to the process, or less $SO_3$ needs to be added to obtain a given quality to caprolactam.

One way of obtaining cyclohexanone oxime having a water content of less than 2 wt. % is drying cyclohexanone oxime with a high water content for example with inert gas. A preferred way of obtaining cyclohexanone oxime having a water content of less than 2 wt. % is a process in which cyclohexanone oxime is obtained by a) preparing an organic medium comprising cyclohexanone oxime dissolved in an organic solvent, and b) separating, by distillation, cyclohexanone oxime from said organic medium.

Preparing an organic medium comprising cyclohexanone oxime dissolved in an organic solvent is preferably carried out by contacting in a reaction zone in countercurrent flow a stream of a solution of cyclohexanone in an organic solvent which is also a solvent for the cyclohexanone oxime and a stream of an a phosphate buffered, aqueous solution of hydroxylammonium; and withdrawing from the reaction zone an organic medium of cyclohexanone oxime dissolved in said organic solvent. Particularly suitable organic solvent for use in the process for preparing cyclohexanone oxime are toluene and benzene. Preferably toluene is used as organic solvent. The phosphate buffered, aqueous reaction medium is preferably continuously recycled between a hydroxylammonium synthesis zone and a cyclohexanone oxime synthesis zone. In the hydroxylammonium synthesis zone hydroxylammonium is formed by catalytic reduction of nitrate ions or nitric oxide with hydrogen. In the cyclohexanone oxime synthesis zone, hydroxylammonium formed in the hydroxylammonium synthesis zone reacts with cyclohexanone to form cyclohexanone oxime. The cyclohexanone oxime can then be separated from the aqueous reaction medium which is recycled to the hydroxylammonium synthesis zone. An organic medium comprising the formed cyclohexanone oxime dissolved in said organic solvent is withdrawn from the reaction zone, and may be distilled to recover cyclohexanone oxime having for instance a water content less than 2 wt. %, less than 1 wt. %, less than 0.2 wt. % or even less than 0.1 wt. %.

The organic medium generally comprises cyclohexanone oxime, said organic solvent and optionally cyclohexanone. In case the organic medium comprises cyclohexanone, the concentration of cyclohexanone in the organic medium may be higher than 0.1 wt. %, preferably higher than 0.5 wt. %, most preferably higher than 1 wt. %. The concentration of cyclohexanone in the organic medium may be lower than 10 wt. %, preferably lower than 5 wt. %. The concentration of cyclohexanone oxime in the organic medium may be higher than 5 wt. %, preferably higher than 10 wt. %, more preferably higher than 25 wt. %, and may be lower than 60 wt. %, preferably lower than 50 wt. %. The concentration of organic solvent in the organic medium may be higher than 40 wt. %, preferably higher than 50 wt. %, and may be lower than 95 wt. %, preferably lower than 90 wt. %.

In said preferred way of obtaining cyclohexanone oxime having a water content of less than 2 wt. %, separating cyclohexanone oxime from said organic medium is effected by distillation. The distillation can be effected in any suitable manner. The distillation may be carried out using any suitable column or combination of columns. In one embodiment, the separation by distillation comprises distilling the organic medium to obtain organic solvent as a distillate (overhead product) and cyclohexanone oxime as a bottom product. The cyclohexanone oxime, e.g. obtained as a bottom product may for instance comprise less than 2 wt. %, preferably less than 1 wt. %, more preferably less than 0.2 wt. %, more preferably less than 0.1 wt. % of water, and may be fed to the reaction mixture(s). The distillation may be carried out at any suitable temperature, for instance between 35 and 115° C., preferably between 50 and 100° C., and at any suitable pressure, for instance between 0.006 and 0.020 MPa, preferably between 0.012 and 0.020 MPa. As used herein, the temperature refers to the temperature in the top of a column in which the distillation is effected. As used herein, the pressure refers to the pressure in the top of a column in which the distillation is effected. Examples for effecting the distillation are described in GB-A-1303739 and EP-A-5291.

In a more stage rearrangement, the molar ratio M is preferably different in each reaction mixture. The molar ratio M in the first, second and, if applicable, third reaction mixture will, as used herein, be referred to as $M(1)$, $M(2)$ and $M(3)$ respectively. The concentration $SO_3$ in the first, second, and, if applicable, third reaction mixture will, as used herein, be referred to as $C_{SO3}(1)$, $C_{SO3}(2)$ and $C_{SO3}(3)$. The temperature in the first, second and, if applicable, third reaction mixture will, as used herein, be referred to as $T(1)$, $T(2)$ and $T(3)$ respectively. As used herein, the values for M, the $SO_3$ concentration, and the temperature refer in particular to the value in the reaction mixture obtained after feeding of the cyclohexanone oxime into the reaction mixture.

Preferred values for M and the $SO_3$ concentration can be obtained by feeding cyclohexanone oxime to the different stages in appropriate amounts with appropiate amounts water, and by applying appropriate quantities of oleum of appropriate $SO_3$ concentration.

Preferably, $M(2)$ is lower than $M(1)$. Preferably $M(3)$ is lower than $M(2)$.

In a preferred embodiment, $M(1)$ is between 1.2 and 2.2, preferably between 1.4 and 1.9, more preferably between 1.5 and 1.8. Preferably, $CSO_3(1)$ is preferably between 9 and 20 wt. %, more preferably higher than 10 wt. % and even more preferably higher than 12 wt. %. Increased values for $C_{SO3}(1)$ have the advantage that $C_{SO3}(2)$ can be kept high in the second reaction mixture without having to feed oleum to the second reaction mixture. $C_{SO3}(1)$ is preferably less than 18 wt. % and even more preferably less than 17 wt. %. Preferably $T(1)$ is between 70 and 130° C., more preferably between 70 and 120° C.

In a preferred embodiment $M(2)$ in a two stage rearrangement is between 1.0 and 1.4, preferably between 1.2 and 1.4 and $M(2)$ in a three stage rearrangement is between 1.0 and 1.6, preferably between 1.2 and 1.4. Preferably, $C_{SO3}(2)$ is between 9 and 20 wt. %, more preferably higher than 10 wt. %, more preferably higher than 12 wt. %. Increased concentrations of $C_{SO3}(2)$ within the abovementioned ranges for M(2) were surprisingly found to result in significantly higher yields. $C_{SO3}(2)$ is preferably less than 18 wt. % and even more preferably less than 16 wt. %. Preferably T(2) is between 70 and 130° C. and more preferably between 80 and 120° C.

In a preferred embodiment M(3) is between 1.0 and 1.4 and preferably between 1.0 and 1.3. Preferably, $C_{SO3}(3)$ is between 9 and 18 wt. %, preferably higher than 10 wt. %, more preferably higher than 11 wt. %. Increased concentrations of $C_{SO3}(3)$ within the abovementioned ranges for M(3) were surprisingly found to result in significantly higher yields. $C_{SO3}(3)$ is preferably less than 17 wt. % and even more preferably less than 16 wt. %. Preferably T(3) is between 70 and 130° C. and more preferably between 80 and 120° C.

Preferably, in such multi-stage rearrangement, the rearrangement is carried out in a plurality of stages connected in series in which the molar ratio M of the reaction mixture preferably decreases in each further stage. Preferably, the rearrangement is carried out in at least two stages and more preferably in at least three stages connected in series. Oleum may be fed into the reaction mixture in any suitable way. Preferably all oleum applied is fed into the first reaction mixture, while preferably cyclohexanone oxime is fed to the first, second, and, if applicable, to the third reaction mixture. Preferably, the amount of cyclohexanone oxime fed to the first reaction mixture is larger than the amount of cyclohexanone oxime fed to the second reaction mixture, and, if applicable, preferably the amount of cyclohexanone oxime fed to the second reaction mixture is larger than the amount of cyclohexanone oxime fed to the third reaction mixture. This is advantageous as, due to the lower molar ratio in each further stage, the yield to caprolactam decreases in each further stage. Feeding cyclohexanone oxime to each stage with an amount decreasing from each stage results in that the overall high yield to caprolactam is maintained with a comparable lower ammonium sulfate by-product formation. Preferably, from 60 to 95 wt. % of the total amount of cyclohexanone oxime fed into the first, second and, if applicable, third reaction mixture, is fed into the first reaction mixture. Preferably, from 5 to 40 wt. % of the total amount of cyclohexanone oxime fed into the first, second and, if applicable, third reaction mixture is fed into the second reaction mixture. If applicable, preferably, from 2 to 15 wt. % of the total amount of cyclohexanone oxime fed into the first, second and third reaction mixture is fed into the third reaction mixture.

Preferably, one parts by volume of cyclohexanone oxime is continuously introduced into at least 10 parts by volume, more preferably at least 20 parts by volume of reaction mixture.

Cyclohexanone oxime is preferably fed to the reaction mixture in the form of a liquid melt.

Cyclohexanone oxime (melt) and, separately therefrom, oleum are preferably introduced via dividers. Preferably cyclohexanone oxime is intensively mixed with the reaction mixture. Suitable methods for admixture cyclohexanone oxime with the reaction mixture are for example described in U.S. Pat. No. 3,601,318 and EP-A-15617. In a preferred embodiment of the invention, cyclohexanone oxime is admixed to the reaction mixture using a mixing device as depicted in FIG. 2. In FIG. 2, the mixing device comprises a cylindrical tube 101 that in first part 101a narrows to throat 101b, and beyond throat 101b widens in a second part 101c. The second part 101c of the tube is connected to a second tube 102. In the throat openings 103 are present which are in connection with feed chamber 104. Cyclohexanone oxime is supplied via feed chamber 104, and fed into reaction mixture through openings 103. The mixing device comprises closures 105 with which openings 103 can be opened and closed independently. The mixing device also comprises a baffle 106 opposite to the exit of tube 101. The tube opens into collecting vessel B, having walls 110, overflow 111, and outlet 112. Reaction mixture leaving tube 102 is collected in the collecting vessel B, and leaves collecting vessel B partly via line 112 to be further circulated, and partly via overflow 111 to be fed into a subsequent reaction mixture or for the recovery of caprolactam. In a more preferred embodiment of the invention, the mixing device comprises (i) a tube through which the reaction mixture can flow, and (ii) channels disposed around the tube, said channels opening into the tube, said process comprising: passing the reaction mixture through the tube, and feeding the cyclohexanone oxime into the reaction mixture through one or more of said channels, wherein Re of the reaction mixture>5000, preferably higher than 10.000, Re being the Reynolds number as defined by $\rho \cdot V \cdot D / \eta$, wherein $\rho$=density (in kg/m³) of the reaction mixture that is fed to the tube V=velocity of the reaction mixture, V being defined as W/A, wherein W is the flow rate (in m³/s) of the reaction mixture that is fed into the tube and A is the cross section area of the tube (in m²) at the level where said channels open into the tube.

D=diameter of the tube at the level where said channels open into the tube (in m).

$\eta$=viscosity of the reaction mixture that is fed into the tube (in Pa·s).

The recovery of caprolactam from the reaction mixture obtained in (the last stage of) the Beckmann rearrangement may be performed by known methods. Preferably, the reaction mixture obtained in (the last stage of) the Beckmann rearrangement is neutralized with ammonia in water and the ammonium sulfate thus formed is removed from the caprolactam solution. The caprolactam solution may be purified by known procedures.

DESCRIPTION OF PREFERRED EMBODIMENT

FIG. 1 shows a preferred set-up for a rearrangement in three stages comprising a first circulation system, a second circulation system and a third circulation system. The first circulation system comprises mixing device A1, collecting vessel B1, pump C1 and cooler D1, and a first reaction mixture is kept in circulation via line 1. The second circulation system comprises mixing device A2, collecting vessel B2, pump C2 and cooler D2, and a second reaction mixture is kept in circulation via line 11. The third circulation system comprises mixing device A3, collecting vessel B3, pump C3 and cooler D3, and a third reaction mixture is kept in circulation via line 21. Cyclohexanone oxime and oleum are fed into the first reaction mixture via line 2 and line 3 respectively. A portion of the first reaction mixture is withdrawn from collecting vessel B1 via line 4 and fed into the second reaction mixture. Cyclohexanone oxime is fed into the second reaction mixture via line 12. A portion of the second reaction mixture is withdrawn from collecting vessel B2 via line 14 and fed into the third reaction mixture. Cyclohexanone oxime is fed to the third reaction mixture via line 22. A portion of the third reaction mixture is withdrawn from collecting vessel B3 via line 24. The process is carried out continuously.

FIG. 2 shows a mixing device that is preferably used as mixing device A1, mixing device A2, and mixing device A3.

The following specific examples are to be construed as merely illustrative, and not limitative, of the remainder of the disclosure.

In the examples the yield to caprolactam was determined as follows: Samples were taken from the reaction mixture leaving the last stage of the rearrangement. The yield (amount of caprolactam formed per amount of cyclohexanone oxime fed to the reaction mixture) was determined as follows: To a first part (0.2 g) of each sample concentrated sulfuric acid (20 ml, 96wt%) was added, as well as 15 g $K_2SO_4$ and 0.7 g HgO. The nitrogen content of the resulting acidic mixture was determined using the Kjeldahl Method, from which the molar concentration of nitrogen in the first part of the sample (TN) was calculated. A second part of each sample is extracted with chloroform. This method is based on the fact that caprolactam enters the chloroform phase. The impurities stay in the water phase. The extracted aqueous phase is analyzed for its nitrogen content by the Kjeldahl Method, from which the molar concentration of nitrogen in the second part of the sample (RN) was calculated. The yield is calculated as follows:

$$\% \text{ yield} = \left(1 - \frac{RN}{TN}\right) \times 100$$

The absorbance at 290 nm ($E_{290}$), used as quality specification of the obtained caprolatam, was determined as follows:

The reaction mixture leaving the last stage of the rearrangement was neutralized with ammonia, and the resulting caprolactam-containing aqueous phase was separated. The absorbance of the separated caprolactam-containing aqueous phase was measured at a wavelength of 290 nm using a 1 cm cuvette (calculated for a 70 wt. % aqueous caprolactam solution).

EXAMPLES I-V

In a laboratory setup, in a 0.5 l baffled reactor equipped with a turbine type stirrer, cyclohexanone oxime (containing less than 100 ppm water) and oleum were continuously added to a reaction mixture comprising caprolactam, sulfuric acid and sulfur trioxide and reaction mixture is continuously withdrawn. The amount of reaction mixture withdrawn is equivalent to the amount of cyclohexanone oxime and oleum introduced into the reaction mixture. Cyclohexanone oxime was intensively mixed with the reaction mixture. In each experiment the molar ratio M of the reaction mixture was kept around 1.2.

The temperature at which the experiments were performed was 95° C. The $SO_3$ content (% $SO_3$) of the reaction mixture was varied form 5 to 15% by using oleum with different $SO_3$ content. The results are given in Table I.

Table I below shows that at a given molar ratio the yield to caprolactam increases and the quality improves at increasing $SO_3$ amount in the reaction mixture.

TABLE I

| % $SO_3$ | Yield | Extinction at 290 nm (1 cm/70 wt. %) |
|---|---|---|
| 4.5 | 97.73 | 3.7 |
| 6.7 | 97.95 | 3.2 |
| 9.4 | 98.21 | 2.50 |
| 13.6 | 98.51 | 1.42 |

EXAMPLE VI-X

Examples I-V were repeated with the difference that the temperature at which the experiments were performed was 75° C. The results are given in Table II. Table II below shows that at a given molar ratio the yield to caprolactam increases and the quality improves at increasing $SO_3$ amount in the reaction mixture.

TABLE II

| % $SO_3$ | Yield | Extinction at 290 nm (1 cm/70 wt. %) |
|---|---|---|
| 3.4 | 97.66 | 2.8 |
| 6.3 | 97.85 | 2.2 |
| 9.9 | 98.23 | 1.27 |
| 15.2 | 99.04 | 0.3 |

EXAMPLE XI

A set-up was used as depicted in FIGS. 1 and 2. To the first stage of a rearrangement system 7.1 t/hr oxim containing less than 100 ppm water is fed (2) and 9.8 t/hr oleum containing 29 wt. % $SO_3$ (3) is fed to the first stage. The temperature in the pump vessel (C1) is maintained at 102° C. by circulating the first reaction mixture at a rate of 400 t/hr over a cooler (D1) in which its temperature is lowered to 77° C. The oxime is mixed into the circulating first reaction mixture through a mixing device (A1) having a throat diameter of 51 mm (101b) and the mixing device was provided with 16 channels (diameter 3 mm). Cyclohexanone oxime was fed through 8 channels (8 of the channels being in closed position). The velocity of the circulating mixture in the throat is 40 m/s and the velocity at which cyclohexanone oxime is fed to the circulating reaction mixutre is 41 m/s. The reactor discharge (4) is sent to the second stage of the rearrangement system where 1.9 t/hr oxime of identical origine is added (12). In the second and third stage of the rearrangement system the oxime is mixed into the circulating second and third reaction mixture through a mixing device (A2 and A3 respectively) as used in the first stage but of which the dimensions are adapted to the lower throughput in the second and third stage. Circulation rate is 150 t/hr and cooler (D2) outlet temperature is 72° C. and the reactor operates at 86° C. Finally the reactor discharge (14) is sent to the third stage of the rearrangement system where 1.1 t/hr oxime is added (22). Operating temperature is again 86° C. controlled by circulating rate of 100 t/hr and cooler (D3) outlet temperature of 76° C. The molar ratio M of the first, second and third reaction mixture respectively is 1.70, 1.35 and 1.20 respectively. The $SO_3$ content of the first, second and third reaction mixture was 16.7, 15.0 and 14.3 wt. % respectively. The yields in the discharge of each rearrangement reactor were determined using the above given method. These yields are overall yields and through calculation the yield of the second and third step is determined. The overall yield of the 3-stage rearrangement system was 99.5%. The yield of the third stage was 98.9%. The extinction at 290 nm (determined as given above) was 0.365.

Comparative Experiment A

Example XI was repeated with the difference that cyclohexanone oxime with 4.5 wt. % water was used and that 9.3 t/hr oleum containing 29 wt. % $SO_3$. To ensure similar oleum to oxime consumption ratios the oleum feed was adjusted in a way that the molar ratios measured in each of the three stages were close or identical to the values from Example XI. The molar ratio M of the third reaction mixture is 1.20. The $SO_3$ content of the first, second and third reaction mixture respectively was 7.9, 4.9 and 3.4 wt. % respectively. The yields in the discharge of each rearrangement reactor were determined. These yields are overall yields and through calculation the yield of the second and third stage is determined. The overall yield of the 3-stage rearrangement system was 99.3%. The yield of the third step was 98.3%. The extinction at 290 nm (determined as given above) was 1.036.

The invention claimed is:

1. Process for preparing caprolactam in a multi-stage Beckmann rearrangement of cyclohexanone oxime by feeding cyclohexanone oxime to a reaction mixture comprising (i) sulfuric acid (ii) $SO_3$ and (iii) caprolactam, wherein in at least a last stage of the rearrangement (1) the $SO_3$ content of the reaction mixture is between 9 and 20 wt. % and (2) the molar ratio M of the reaction mixture defined as $(n_{SO3} + n_{H2SO4})/n_{cap}$ is between 1 and 1.4, wherein nSO$_3$=quantity of $SO_3$ in reaction mixture, in mol
nH$_{2SO4}$=quantity of $H_2SO_4$ in reaction mixture, in mol
$n_{cap}$=quantity of caprolactam in reaction mixture, in mol.

2. Process according to claim 1, wherein the molar ratio M of the reaction mixture in at least the last stacie of the rearrangement is between 1.15 and 1.4 and the $SO_3$ content of the reaction mixture in at least the last stage of the rearrangement is between 10 and 18 wt. %.

3. Process according to claim 1, wherein the process is a continuous process comprising a) feeding (i) oleum and (ii) cyclohexanone oxime into a first reaction mixture comprising caprolactam, sulfuric acid and $SO_3$,
b) feeding (iii) a portion of the first reaction mixture and (iv) cyclohexanone oxime into a second reaction mixture comprising caprolactam, sulfuric acid and $SO_3$, wherein the molar ratio M of the second reaction mixture is between 1.0 and 1.4 and the $SO_3$ content of the second reaction mixture is between 9 and 20 wt. %,
c) withdrawing a portion of the second reaction mixture.

4. Process according to claim 1, wherein the process is a continuous process comprising a) feeding (i) oleum and (ii) cyclohexanone oxime into a first reaction mixture comprising caprolactam, sulfuric acid and $SO_3$,
b) feeding (iii) a portion of the first reaction mixture and (iv) cyclohexanone oxime into a second reaction mixture comprising caprolactam, sulfuric acid and $SO_3$,
(c) withdrawing a portion of the second reaction mixture,
d) feeding (v) a portion of the second reaction mixture and (vi) cyclohexanone oxime into a third reaction mixture comprising caprolactam, sulfuric acid and $SO_3$, wherein the molar ratio M of the third reaction mixture is between 1.0 and 1.4 and the $SO_3$ content of the third reaction mixture is between 9 and 20 wt. %, and
e) withdrawing a portion of the third reaction mixture.

5. Process according to claim 1, wherein the cyclohexanone oxime has a water content of less than 2% by weight.

6. Process according to claim 1, wherein the cyclohexanone oxime has a water content of less than 1 wt. % by weight.

7. Process according to claim 1, wherein the cyclohexanone oxime is obtained by a) preparing an organic medium comprising cyclohexanone oxime dissolved in an organic solvent, and
b) separating, by distillation, cyclohexanone oxime from said organic medium.

* * * * *